US010631740B2

(12) United States Patent
Romesburg

(10) Patent No.: US 10,631,740 B2
(45) Date of Patent: Apr. 28, 2020

(54) REDUCTION OF PHYSIOLOGICAL METRIC ERROR DUE TO INERTIAL CADENCE

(71) Applicant: Valencell, Inc., Raleigh, NC (US)

(72) Inventor: Eric Douglas Romesburg, Chapel Hill, NC (US)

(73) Assignee: VALENCELL, INC., Raleigh, NC (US)

(*) Notice: Subject to any disclaimer, the term of this patent is extended or adjusted under 35 U.S.C. 154(b) by 0 days.

(21) Appl. No.: 16/694,402

(22) Filed: Nov. 25, 2019

(65) Prior Publication Data

US 2020/0085314 A1 Mar. 19, 2020

Related U.S. Application Data

(63) Continuation of application No. 16/146,362, filed on Sep. 28, 2018, now Pat. No. 10,542,896, which is a continuation of application No. 14/370,689, filed as application No. PCT/US2012/071594 on Dec. 24, 2012, now Pat. No. 10,349,844.

(60) Provisional application No. 61/586,884, filed on Jan. 16, 2012.

(51) Int. Cl.
A61B 5/024 (2006.01)
A61B 5/00 (2006.01)
A61B 5/11 (2006.01)

(52) U.S. Cl.
CPC ............. A61B 5/024 (2013.01); A61B 5/112 (2013.01); A61B 5/6817 (2013.01); A61B 5/721 (2013.01); A61B 2562/0219 (2013.01); A63B 2220/17 (2013.01); A63B 2230/04 (2013.01)

(58) Field of Classification Search
CPC ......... A61B 5/024; A61B 5/721; A61B 5/112; A61B 5/0205; A61B 5/021
See application file for complete search history.

(56) References Cited

U.S. PATENT DOCUMENTS

| | | | |
|---|---|---|---|
| 3,636,617 | A | 1/1972 | Schmidt et al. |
| 3,704,706 | A | 12/1972 | Herczfeld et al. |
| 4,672,976 | A | 6/1987 | Kroll |
| 4,830,014 | A | 5/1989 | Goodman et al. |
| 4,952,928 | A | 8/1990 | Carroll et al. |
| 4,955,379 | A | 9/1990 | Hall |

(Continued)

FOREIGN PATENT DOCUMENTS

| | | |
|---|---|---|
| CN | 1545979 A | 11/2004 |
| CN | 101317188 A | 12/2008 |

(Continued)

OTHER PUBLICATIONS

Pierpont, G. et al., "Assessing Autonomic Function by Analysis of Heart Rate Recovery from Exercise in Healthy Subjects", The American Journal of Cardiology, Vo. 94, Jul. 1, 2004, pp. 64-68, Excerpta Medica, Inc.

(Continued)

Primary Examiner — Mohamed Charioui
(74) Attorney, Agent, or Firm — Coats & Bennett, PLLC

(57) ABSTRACT

The heart rate monitor disclosed herein removes a step rate component from a measured heart rate by using one or more filtering techniques when the step rate is close to the heart rate. In general, a difference between the step rate and the heart rate is determined, and the step rate is filtered from the heart rate based on a function of the difference.

18 Claims, 10 Drawing Sheets

(56) References Cited

U.S. PATENT DOCUMENTS

| | | |
|---|---|---|
| 5,139,025 A | 8/1992 | Lewis et al. |
| 5,226,417 A | 7/1993 | Swedlow et al. |
| 5,243,992 A | 9/1993 | Eckerle et al. |
| 5,297,548 A | 3/1994 | Pologe |
| 5,299,570 A | 4/1994 | Hatschek |
| 5,396,893 A | 3/1995 | Oberg et al. |
| 5,448,082 A | 9/1995 | Kim |
| 5,482,036 A | 1/1996 | Diab et al. |
| 5,494,043 A | 2/1996 | O'Sullivan et al. |
| 5,503,016 A | 3/1996 | Koen |
| 5,575,284 A | 11/1996 | Athan et al. |
| 5,673,692 A | 10/1997 | Schulze et al. |
| 5,797,841 A | 8/1998 | Delonzor et al. |
| 5,817,008 A | 10/1998 | Rafert et al. |
| 5,807,267 A | 11/1998 | Bryars et al. |
| 5,846,190 A | 12/1998 | Woehrle |
| 5,853,005 A | 12/1998 | Scanlon |
| 5,906,582 A | 5/1999 | Kondo et al. |
| 5,908,396 A | 6/1999 | Hayakawa et al. |
| 5,941,837 A | 8/1999 | Amano et al. |
| 5,954,644 A | 9/1999 | Dettling et al. |
| 5,964,701 A | 10/1999 | Asada et al. |
| 6,022,748 A | 2/2000 | Charych et al. |
| 6,042,549 A | 3/2000 | Amano et al. |
| 6,067,462 A | 5/2000 | Diab et al. |
| 6,198,394 B1 | 3/2001 | Jacobsen et al. |
| 6,241,684 B1 | 6/2001 | Amano et al. |
| 6,267,721 B1 | 7/2001 | Welles |
| 6,393,311 B1 | 5/2002 | Edgar, Jr. et al. |
| 6,443,890 B1 | 9/2002 | Schulze et al. |
| 6,527,711 B1 | 3/2003 | Stivoric et al. |
| 6,608,562 B1 | 8/2003 | Kimura et al. |
| 6,656,151 B1 | 12/2003 | Blatter |
| 6,702,752 B2 | 3/2004 | Dekker |
| 6,721,584 B2 | 4/2004 | Baker, Jr. et al. |
| 6,725,072 B2 | 4/2004 | Steuer et al. |
| 6,745,061 B1 | 6/2004 | Hicks et al. |
| 6,748,254 B2 | 6/2004 | O'Neil et al. |
| 6,801,799 B2 | 10/2004 | Mendelson |
| 6,898,451 B2 | 5/2005 | Wuori |
| 6,995,665 B2 | 2/2006 | Appelt et al. |
| 6,996,427 B2 | 2/2006 | Ali et al. |
| 6,997,879 B1 | 2/2006 | Turcott |
| 7,018,338 B2 | 3/2006 | Vetter et al. |
| 7,107,088 B2 | 9/2006 | Aceti |
| 7,113,815 B2 | 9/2006 | O'Neil et al. |
| 7,144,375 B2 | 12/2006 | Kosuda |
| 7,190,986 B1 | 3/2007 | Hannula et al. |
| 7,209,775 B2 | 4/2007 | Bae et al. |
| 7,336,982 B2 | 2/2008 | Yoo |
| 7,378,954 B2 | 5/2008 | Wendt |
| 7,438,688 B2 | 10/2008 | Kobayashi et al. |
| 7,539,533 B2 | 5/2009 | Tran |
| 7,962,308 B2 | 6/2011 | Makino |
| 8,055,469 B2 | 11/2011 | Kulach et al. |
| 8,109,874 B2 * | 2/2012 | Kong ............... A61B 5/0205 600/300 |
| 8,923,941 B2 | 12/2014 | LeBoeuf et al. |
| 9,005,129 B2 | 4/2015 | Venkatraman et al. |
| 9,044,180 B2 | 6/2015 | LeBoeuf et al. |
| 9,717,412 B2 * | 8/2017 | Roham ............... A61B 8/0866 |
| 2002/0013538 A1 | 1/2002 | Teller |
| 2003/0065269 A1 | 4/2003 | Vetter et al. |
| 2003/0109791 A1 | 6/2003 | Kondo et al. |
| 2003/0176815 A1 | 9/2003 | Baba et al. |
| 2003/0181798 A1 | 9/2003 | Al-Ali |
| 2003/0233051 A1 | 12/2003 | Verjus et al. |
| 2003/0236647 A1 | 12/2003 | Yoon et al. |
| 2004/0004547 A1 | 1/2004 | Appelt et al. |
| 2004/0039254 A1 | 2/2004 | Stivoric et al. |
| 2004/0054291 A1 | 3/2004 | Schulz et al. |
| 2004/0059236 A1 | 3/2004 | Margulies et al. |
| 2004/0186387 A1 | 9/2004 | Kosuda et al. |
| 2004/0186695 A1 | 9/2004 | Aoshima et al. |
| 2004/0178913 A1 | 11/2004 | Penuela et al. |
| 2004/0236233 A1 | 11/2004 | Kosuda et al. |
| 2004/0242976 A1 | 12/2004 | Abreu |
| 2004/0254501 A1 | 12/2004 | Mault |
| 2005/0007582 A1 | 1/2005 | Villers et al. |
| 2005/0043652 A1 | 2/2005 | Lovett et al. |
| 2005/0059870 A1 | 3/2005 | Aceti |
| 2005/0075542 A1 | 4/2005 | Goldreich |
| 2005/0192516 A1 | 9/2005 | Takiguchi et al. |
| 2005/0209516 A1 | 9/2005 | Fraden |
| 2005/0212405 A1 | 9/2005 | Negley |
| 2005/0228463 A1 | 10/2005 | Mac et al. |
| 2005/0245839 A1 | 11/2005 | Stivoric et al. |
| 2006/0064037 A1 | 3/2006 | Shalon et al. |
| 2006/0084879 A1 | 3/2006 | Nazarian et al. |
| 2006/0178588 A1 * | 8/2006 | Brody ............... A61B 5/02405 600/513 |
| 2006/0258927 A1 | 11/2006 | Edgar, Jr. et al. |
| 2007/0016086 A1 | 1/2007 | Inukai et al. |
| 2007/0027367 A1 | 2/2007 | Oliver et al. |
| 2007/0116314 A1 | 5/2007 | Grilliot et al. |
| 2007/0123763 A1 | 5/2007 | Al-Ali et al. |
| 2007/0135717 A1 | 6/2007 | Uenishi et al. |
| 2007/0197881 A1 | 8/2007 | Wolf et al. |
| 2008/0076972 A1 | 3/2008 | Dorogusker et al. |
| 2008/0081972 A1 | 4/2008 | Debreczeny |
| 2008/0132798 A1 | 6/2008 | Hong et al. |
| 2008/0133699 A1 | 6/2008 | Craw et al. |
| 2008/0146890 A1 | 6/2008 | LeBoeuf et al. |
| 2008/0154098 A1 | 6/2008 | Morris et al. |
| 2008/0177162 A1 | 7/2008 | Bae et al. |
| 2008/0200774 A1 | 8/2008 | Luo |
| 2008/0269625 A1 | 10/2008 | Halperin et al. |
| 2009/0010461 A1 | 1/2009 | Klinghult et al. |
| 2009/0023556 A1 | 1/2009 | Daly |
| 2009/0097689 A1 | 4/2009 | Prest et al. |
| 2009/0105556 A1 | 4/2009 | Fricke et al. |
| 2009/0112111 A1 | 4/2009 | Shimizu |
| 2009/0131761 A1 | 5/2009 | Moroney, III et al. |
| 2009/0281435 A1 | 11/2009 | Ahmed et al. |
| 2009/0287067 A1 | 11/2009 | Dorogusker et al. |
| 2009/0306736 A1 | 12/2009 | Dobak, III |
| 2010/0189209 A1 | 7/2010 | O'Rourke |
| 2010/0274109 A1 * | 10/2010 | Hu ............... A61B 5/02405 600/310 |
| 2011/0022352 A1 | 1/2011 | Fujita et al. |
| 2011/0178759 A1 | 7/2011 | Uchida |
| 2012/0197093 A1 | 8/2012 | LeBoeuf et al. |
| 2012/0303319 A1 | 11/2012 | Kirkeby |
| 2013/0006583 A1 | 1/2013 | Weast et al. |

FOREIGN PATENT DOCUMENTS

| | | |
|---|---|---|
| CN | 101910846 A | 12/2010 |
| CN | 101980659 A | 2/2011 |
| CN | 102168986 A | 8/2011 |
| CN | 102297701 A | 12/2011 |
| CN | 102435203 A | 5/2012 |
| EP | 0729726 A2 | 9/1996 |
| EP | 1354553 A1 * | 10/2003 ......... A61B 5/02416 |
| EP | 1354553 A1 | 10/2003 |
| EP | 2229880 A1 | 9/2010 |
| EP | 2182839 B1 | 10/2011 |
| JP | H110258039 | 9/1998 |
| JP | 2004283228 A | 10/2004 |
| JP | 2004358271 A | 12/2004 |
| JP | 2005040261 A | 2/2005 |
| JP | 2005270544 A | 10/2005 |
| WO | 0021435 A1 | 4/2000 |
| WO | 0044274 | 8/2000 |
| WO | 2005010568 A2 | 2/2005 |
| WO | 2005036212 A2 | 4/2005 |
| WO | 2006009830 A2 | 1/2006 |
| WO | 2007013054 A1 | 2/2007 |
| WO | 2007122375 A2 | 11/2007 |
| WO | 2011026669 A | 3/2011 |
| WO | 2011105914 A1 | 9/2011 |
| WO | 2013038296 A1 | 3/2013 |

(56) References Cited

FOREIGN PATENT DOCUMENTS

| | | |
|---|---|---|
| WO | 2013109389 A1 | 7/2013 |
| WO | 2014109982 A2 | 7/2014 |

OTHER PUBLICATIONS

Coote, J., "Recovery of Heart Rate Following Intense Dynamic Exercise", Experimental Physiology—Review Article, Exp Physical 95.3, Mar. 1, 2010, pp. 431-440, The Physiological Society.

Wise, K., "Integrated sensors, MEMS, and microsystems: Reflections on a fantastic voyage," Sensors and Actuators A, vol. 136, Feb. 5, 2007, pp. 39-50.

Gigoi, B.P., et al., "Integration Technology for MEMS Automotive Sensors," 28th Annual Conference of the IEEE, Jan. 1, 2002, pp. 2712-2717.

Ko, W., "Trends and frontiers of MEMS," Sensors and Actuators A, vol. 136, Feb. 1, 2007, pp. 62-67.

Barbour, N., "Inertial Sensor Technology Trends," IEEE Sensors Journal, vol. 1, No. 4, Dec. 1, 2001, pp. 332-339.

Vigario, R., "Independent Component Approach to the Analysis of EEG and MEG Recordings," IEEE Transactions on Biomedical Engineering, vol. 47, No. 5, May 1, 2000, pp. 589-593.

Mayer-Kress, G., "Localized Measures for Nonstationary Time-Series of Physiological Data," Integr. Physiol. Behav. Sci., vol. 29, No. 3, Jul. 1, 1994, pp. 205-210.

Shaw, G.A., et al., "Warfighter Physiological and Environmental Monitoring: A Study for the U.S. Army Research Institute in Environmental Medicine and the Soldier Systems Center," Lincoln Laboratory, Massachusetts Institute of Technology, Lexington, MA., Nov. 1, 2004, pp. 1-128.

Laguna, P., et al., "Power Spectral Density of Unevenly Sampled Data by Least-Square Analysis: Performance and Application to Heart Rate Signals," IEEE Transactions on Biomedical Engineering, vol. 45, No. 6, Jun. 1, 1998, pp. 698-715.

Richardson, J.E., "Physiological Responses of Firefighters Wearing Level 3 Chemical Protective Suits While Working in Controlled Hot Environments," J. Occup. Environ. Med., vol. 43, No. 12, Dec. 1, 2001, pp. 1064-1072.

Scanlon, M., "Acoustic Sensors in the Helmet Detect Voice and Physiology," Proceedings of SPIE, vol. 5071, Jan. 1, 2003, pp. 41-51.

Arnold, M., et al., "Adaptive AR Modeling of Nonstationary Time Series by Means of Kalman Filtering," IEEE Transactions on Biomedical Engineering, vol. 45, No. 5, May 1, 1998, pp. 553-562.

Yan, Y., et al., "Reduction of motion artifact in pulse oximetry by smoothed pseudo Wigner-Ville distribution," Journal of NeuroEngineering and Rehabilitation, vol. 2, No. 3, Mar. 1, 2005, pp. 1-9.

Lee, C.M., et al., "Reduction of Motion Artifacts from Photoplethysmographic Recordings Using a Wavelet Denoising Approach," IEEE EMBS Asian-Pacific Conference on Biomedical Engineering, Jan. 1, 2003, pp. 194-195.

Foo, J.Y.A., "Comparison of wavelet transformation and adaptive filtering in restoring artefact-induced time-related measurement," Biomedical Signal Processing and Control vol. 1, No. 1 (2006), Mar. 24, 2006, pp. 93-98.

Wood, L., et al., "Active Motion Artifact Reduction for Wearable Sensors Using Laguerre Expansion and Signal Separation," Proceedings of the 2005 IEEE Engineering in Medicine and Biology 27th Annual Conference, Shanghai, China, Sep. 1, 2005, pp. 3571-3574.

Cacioppo, J., "Inferring Psychological Significance From Physiological Signals," American Psychologist, vol. 45, No. 1, American Psychological Association, Jan. 1, 1990, pp. 16-28.

Rhee, S., et al., "Artifact-Resistant Power-Efficient Design of Finger-Ring Plethysmographic Sensors," IEEE Transactions on Biomedical Engineering, vol. 48, No. 7, Jul. 1, 2001, pp. 795-805.

Wagner, J., et al., "From Physiological Signals to Emotions: Implementing and Comparing Selected Methods for Feature Extraction and Classification," IEEE Int. Conf. Multimedia and Expo, Jan. 1, 2005, pp. 1-4.

Parkka, J., et al., "Activity Classification Using Realistic Data From Wearable Sensors," IEEE Transactions on Information Technology in Biomedicine, vol. 10, No. 1, Jan. 1, 2006, pp. 119-128.

Georgoulas, G., et al., "Predicting the Risk of Metabolic Acidosis for Newborns Based on Fetal Heart Rate Signal Classification Using Support Vector Machines," IEEE Transactions on Biomedical Engineering, vol. 53, No. 5, May 1, 2006, pp. 875-884.

Liao, W., et al., "A Real-Time Human Stress Monitoring System Using Dynamic Bayesian Network," Proceedings of the 2005 IEEE Computer Society Conference on Computer Vision and Pattern Recognition, Jan. 1, 2005, pp. 1-8.

Moy, M., et al., "Accuracy of uniaxial accelerometer in chronic obstructive pulmonary disease," Journal of Rehabilitation Research and Development, vol. 45, No. 4, Nov. 4, 2008, pp. 611-618.

Moy, M., et al., "Ambulatory Monitoring of Cumulative Free-Living Activity," IEEE Engineering in Medicine and Biology Magazine May/Jun. 2003, May 1, 2003, pp. 89-95.

Ricke, AD, et al. "Automatic Segmentation of Heart Sound Signals Using Hidden Markov Models," IEEE Computers in Cardiology 2005; vol. 32, Jan. 1, 2005, pp. 953-956.

Acharya, R., et al., "Classification of cardiac abnormalities using heart rate signals," Medical and Biological Engineering and Computing 2004, vol. 42, No. 3, Jan. 1, 2004, pp. 288-293.

Allen, F., et al., "Classification of a known sequence of motions and postures from accelerometry data using adapted Gaussian mixture models," Institute of Physics Publishing Physiological Measurement, vol. 27, No. 10, Jul. 25, 2006, pp. 935-951.

Lee, J., et al., "Design of filter to reject motion artifact of pulse oximetry," Computer Standards & Interfaces, vol. 26 (2004), Jul. 4, 2003, pp. 241-249.

Rezek, I.A, et al., "Stochastic Complexity Measures for Physiological Signal Analysis," IEEE Transactions on Biomedical Engineering, vol. 45, No. 9, Sep. 1, 1998, pp. 1186-1191.

Gibbs, P., et al., "Active motion artifact cancellation for wearable health monitoring sensors using collocated MEMS accelerometers," Smart Struct. Mater., International Society for Optics and Photonics, Jan. 1, 2005, pp. 1-9.

Merletti, R., et al., "Advances in processing of surface myoelectric signals: Part 1," Medical and Biological Engineering and Computing, vol. 33, No. 3, May 1, 1995, pp. 362-372.

Asada, H., et al., "Active Noise Cancellation Using MEMS Accelerometers for Motion-Tolerant Wearable Bio-Sensors," Proceedings of the 26th Annual International Conference of the IEEE EMBS, San Francisco, CA, USA, Sep. 1, 2004, pp. 2157-2160.

Newman, A., et al., "Sleep Disturbance, Psychosocial Correlates, and Cardiovascular Disease in 5201 Older Adults: The Cardiovascular Health Study," Journal of American Geriatric Society, vol. 45, No. 1, Jan. 1, 1997, pp. 1-7.

Chan, K.W., et al., "Adaptive Reduction of Motion Artifact from Photoplethysmographic Recordings using a Variable Step-Size LMS Filter," IEEE, Sensors, Jun. 1, 2002, pp. 1342-1346.

Dew, M.A., et al., "Healthy Older Adults' Sleep Predicts All-Cause Mortality at 4 to 19 Years of Follow-Up," Psychosomatic Medicine, vol. 65, Jan. 1, 2003, pp. 63-73.

Gibbs, P., et al., "Reducing Motion Artifact in Wearable Bio-Sensors Using MEMS Accelerometers for Active Noise Cancellation," IEEE American Control Conference, Jun. 1, 2005, pp. 1581-1586.

Yang, B-H, et al., "Development of the ring sensor for healthcare automation," Robotics and Autonomous Systems, vol. 30. Jan. 1, 2000, pp. 273-281.

Healey, J., et al., "Detecting Stress During Real-World Driving Tasks Using Physiological Sensors," IEEE Transactions on Intelligent Transportation Systems, vol. 6, No. 2, Jun. 1, 2005, pp. 156-166.

Hayes, M.J., et al., "A New Method for Pulse Oximetry Possessing Inherent Insensitivity to Artifact," IEEE Transactions on Biomedical Engineering, vol. 48, No. 4, Apr. 1, 2001, pp. 452-461.

Wilson, G., et al., "An Analysis of Mental Workload in Pilots During Flight Using Multiple Psychophysiological Measures," The International Journal of Aviation Psychology, vol. 12, No. 1, May 1, 2001, pp. 3-18.

Baddeley, A.D., "Selective Attention and Performance in Dangerous Environments," HPEE, vol. 5, No. 1, Oct. 1, 2000, pp. 86-91.

(56) References Cited

OTHER PUBLICATIONS

Wilson, G.F., et al., "Performance Enhancement with Real-time Physiologically Controlled Adapative Aiding," Proceedings of the IEA 2000 / HFES 2000 Congress, vol. 44, Jul. 30, 2000, pp. 61-64.
Skinner, M.J., et al., "Workload Issues in Military Tactical Airlift," The International Journal of Aviation Psychology, vol. 12, No. 1, May 1, 2001, pp. 79-93.
Helander, M., "Applicability of Drivers' Electrodermal Response to the Design of the Traffic Environment," Journal of Applied Psychology, vol. 63, No. 4, Jan. 18, 1978, pp. 481-488.
Perala, C.H., "Galvanic Skin Response as a Measure of Soldier Stress," Army Research Laboratory, ARL-TR-4114, May 1, 2007, pp. 1-35.
Zhai, J., et al., "Stress Detection in Computer Users Based on Digital Signal Processing of Noninvasive Physiological Variables," Conf Proc IEEE Eng Med Biol Soc., New York, NY, Aug. 31, 2006; pp. 1355-1358.
Zhai, J., et al., "Stress Recognition Using Non-invasive Technology," FLAIRS Conference, Melbourne Beach, Florida, May 11, 2006, AAAI Press, pp. 395-401.
Endler, J., "Signals, Signal Conditions, and the Direction of Evolution," The American Naturalist, vol. 139, Supplement, Mar. 1, 1992, pp. S125-S153.
Sadeh, A., "The role of actigraphy in sleep medicine," Sleep Medicine Reviews, vol. 6, No. 2, Jan. 1, 2002, pp. 113-124.
Mendelson, Y. et al., "Skin Reflectance Pulse Oximetry: In Vivo Measurements from the Forearm and Calf," Journal of Clinical Monitoring, vol. 7, No. 1, Jan. 1, 1991; pp. 7-12.
Konig, V. et al., "Reflectance Pulse Oximetry—Principles and Obstetric Application in the Zurich System," Journal of Clinical Monitoring and Computing, vol. 14, No. 6, Aug. 1, 1998; pp. 403-412.
Tremper, K. et al., "Pulse Oximetry," Medical Intelligence Article, Anesthesiology, vol. 70, No. 1, Jan. 1, 1989; pp. 98-108.
Haahr, R. et al. "A Wearable 'Electronic Patch' for Wireless Continuous Monitoring of Chronically Diseased Patients," Proceedings of the 5th International Workshop on Wearable and Implantable Body Sensor Networks, Jun. 1-3, 2008; pp. 66-70.
Asada, H. et al., "The Ring Sensor: A New Ambulatory Wearable Sensor for Twenty-Four Hour Patient Monitoring," Proceedings of the 20th Annual Conference of the IEEE Engineering in Medicine and Biology Society, vol. 20, No. 4, Jan. 1, 1998; pp. 1906-1909.
Comtois, G. et al., A Comparative Evaluation of Adaptive Noise Cancellation Algorithms for Minimizing Motion Artifacts in a Forehead-Mounted Wearable Pulse Oximeter, Proceedings of the 29th Annual International Conference of the IEEE EMBS, Lyon, France, Aug. 23, 2007, pp. 1-4.
Gupta, G. Sen et al., "Design of a Low-cost Physiological Parameter Measurement and Monitoring Device," IMTC 2007—Instrumentation and Measurement Technology Conference, Warsaw, Poland, May 1, 2007, pp. 1-6.
Lee, R.G. et al. "A Mobile Care System With Alert Mechanism" IEEE Transactions on Information Technology in Biomedicine, vol. 11, Issue 5, Sep. 1, 2007.
Declaration of Brian W. Anthony, PH.D. in Support of Petition for Inter Partes Review of U.S. Pat. No. 9,044,180, Exhibit 1003, Petition for Inter Partes Review of U.S. Pat. No. 9,044,180; *Apple, Inc.* (Petitioner) v. *Valencell, Inc.* (Patent Owner), IPR 2017-01947, filed Aug. 2-17, 2015, pp. 1-153.
Mendelson, J., et al., "Measurement Site and Photodetector Size Considerations iin Optimizing Power Consumption of a Wearable Reflectance Pulse Oximeter", Proceedings of the 25th Annual International Conference of the IEEE EMBS, Engineering in Medicine and Biology Society, Cancun, Mexico, Sep. 17, 2003, pp. 1-4.
Palder, et al., "Vascular Access for Hemodialysis, Patency rates and Results of Revision", Annals of Surgery, vol. 202, No. 2, Aug. 1, 1985, pp. 1-5.
Spigulis, J., et al., "Wearable wireless photoplethysmography sensors," Biophotonics: Photonic Solutions for Better Health Care, Proceedings of SPIE, vol. 6991, May 1, 2008, pp. 1-7.

Sandberg, M., et al., "Non-invasive monitoring of muscle blood perfusion by photoplethysmography: evaluation of a new application," Acta Physiol Scand., vol. 183, No. 4, Dec. 7, 2004, pp. 335-343.
Sum, K.W., et al. "Vital Sign Monitoring for Elderly at Home: Development of a Compound Sensor for Pulse Rate and Motion," Studies in Health Technology and Informatics, Personalised Health Management Systems, IOS Press, Jan. 1, 2005, pp. 43-50.
Mendelson, Y., et al., "A Wearable Reflectance Pulse Oximeter for Remote Physiological Monitoring," Proceedings of the 28th IEEE EMBS Annual International Conference New York City, USA, Aug. 30, 2006, pp. 912-915.
Jung, W., "Chapter H: OP Amp History," Op Amp Applications Handbook, published by Newnes/Elsevier, Jan. 1, 2005, ISBN-0-7506-7844-5, pp. H.1-H.72.
Texas Instruments, "General Purpose Operational Amplifiers", SLOSS094B, Nov. 1, 1970, pp. 1-19.
Schmitt, O., "A simple differential amplifier," Review of Scientific Instruments vol. 8, No. 126, Apr. 1, 1937, American Institute of Physics, pp. 1-3, available at: http://dx.doi.org/10.1063/1.1752256.
Gray, p, et al., "Recent Advances in Monolithic Operational Amplifier Design," IEEE Transactions on Circuits and Systems, vol. CAS-21, No. 3, May 1, 1974, pp. 317-327.
Horowitz, P., et al., "The Art of Electronics," Second Edition, Cambridge University Press, Jan. 1, 1989, pp. 98-102.
Petition for Inter Partes Review of U.S. Pat. No. 9,044,180; *Apple, Inc.* (Petitioner) v. *Valencell, Inc.* (Patent Owner), IPR 2017-01947, filed Aug. 15, 2017, pp. 1-86.
Buchanan, T., et al., "Neuromusculoskeletal Modeling: Estimation of Muscle Forces and Joint Moments and Movements From Measurements of Neural Command," J Appl Biomech, vol. 20, No. 4, Nov. 1, 2004, pp. 1-34.
Stolwijk, J., "Mathematical Models of Thermal Regulation," Annals of the New York Academy of Sciences, vol. 335, No. 1, Jan. 1, 1980, pp. 98-106.
Wiggs, L, et al., "Sleep patterns and sleep disorders in children with autistic spectrum disorders: insights using parent report and actigraphy," Developmental Medicine and Child Neurology 2004, vol. 46, No. 6, Jan. 1, 2004, pp. 372-380.
Hastings, P.C., "Symptom burden of sleep-disordered breathing in mild-to-moderate congestive heart failure patients," European Respiratory Journal, vol. 27, No. 4, Jan. 1, 2006, pp. 748-755.
Carskadon, M., et al., "Chapter 2—Normal Human Sleep: an Overview," Monitoring and staging human sleep, from Principles and practice of sleep medicine, 5th edition, St. Louis: Elsevier Saunders, Jan. 1, 2011, pp. 1-21.
Critchley, H, "Electrodermal Responses: What Happens in the Brain," The Neuroscientist, vol. 8, No. 2, Jan. 1, 2002, pp. 132-142.
Lang, P., et al., "Looking at pictures: Affective, facial, visceral, and behavioral reactions," Psychophysiology, vol. 30, No. 3, Apr. 22, 1992, pp. 261-273.
Soleymani, M., et al., "Affective Ranking of Movie Scenes Using Physiological Signals and Content Analysis," Proc. 2nd ACM Work. Multimed. Semant., Jan. 1, 2008, pp. 1-8.
Appelhans, B., et al., "Heart Rate Variability as an Index of Regulated Emotional Responding," Review of General Psychology, vol. 10, No. 3, Sep. 15, 2005, pp. 229-240.
Postma, D.S., et al., "The natural history of chronic obstructive pulmonary disease," European Respiratory Monograph, vol. 38, Jan. 1, 2006, pp. 71-83.
Bidargaddi, N., et al., "Ambulatory monitor derived clinical measures for continuous assessment of cardiac rehabilitation patients in a community care model," Pervasive Computing Technologies for Healthcare, 2008 Second International Conference on Pervasive Computing Technolovies for Healthcare, Jan. 30, 2008, pp. 1-5.
Hertzman, A., "The Blood Supply of Various Areas as Estimated by the Photoelectric Plethysmograph," Am J. Physiol, vol. 124, Issue 2, Jul. 18, 1938, pp. 328-340.
Hayes, M., et al., "Artifact reduction in photoplethysmography," Applied Optics, vol. 37, No. 31, Nov. 1, 1998, pp. 7437-7446.
Page, E., et al., "Physiological approach to monitor patients in congestive heart failure: application of a new implantable device-

(56) References Cited

OTHER PUBLICATIONS based system to monitor daily life activity and ventilation," Eurospace, vol. 9, May 3, 2007, pp. 687-693.

Moy, M., et al., "Free-living physical activity in COPD: Assessment with accelerometer and activity checklist," Journal of Rehabilitation Research & Development, vol. 46, No. 2, Nov. 2, 2009, pp. 277-286.

Bennett, T., et al., "Development of Implantable Devices for Continuous Ambulatory Monitoring of Central Hemodynamic Values in Heart Failure Patients," Pacing Clin Electrophysiol. Jun. 2005; vol. 28, No. 6, Jun. 1, 2005, pp. 573-584.

Allen, J., "Photoplethysmography and its application in clinical physiological measurement," Physiological Measurement, vol. 28, Feb. 20, 2007, pp. 1-39.

Webster, J.G. (ed.), "Design of Pulse Oximeters," Institute of Physics Publishing, Philadelphia, PA, Jan. 1, 1997, pp. 1-134.

Webster, J.G. (ed.), "Design of Pulse Oximeters," Institute of Physics Publishing, Philadelphia, PA, Jan. 1, 1997, pp. 135-267.

Shevchenko, Y, et al., "90th Anniversary of the Development by Nikolai S. Korotkoff of the Ascultatory Method of Measuring Blood Pressure," Circulation, vol. 94, No. 2, Jul. 15, 1996, pp. 116-118.

Han, H., et al., "Development of a wearable monitoring device with motion artifact reduced algorithm," International Conference on Control, Automation and Systems 2007, Oct. 17, 2007, Seoul, Korea, pp. 1581-1584.

Petition for Inter Partes Review of U.S. Pat. No. 8,157,730; *Apple, Inc.* (Petitioner) v. *Valencell, Inc.* (Patent Owner), IPR 2017-01701, filed Jun. 30, 2017, pp. 1-89.

Petition for Inter Partes Review of U.S. Pat. No. 8,652,040; *Apple, Inc.* (Petitioner) v. *Valencell, Inc.* (Patent Owner), IPR 2017-01702, filed Jun. 30, 2017, pp. 1-70.

Petition for Inter Partes Review of U.S. Pat. No. 8,652,040; *Apple, Inc.* (Petitioner) v. *Valencell, Inc.* (Patent Owner), IPR 2017-01703, filed Jun. 30, 2017, pp. 1-79.

Petition for Inter Partes Review of U.S. Pat. No. 8,888,701; *Apple, Inc.* (Petitioner) v. *Valencell, Inc.* (Patent Owner), IPR 2017-01704, filed Jun. 30, 2017, pp. 1-84.

Declaration of Dr. Majid Sarrafzadeh, Exhibit 1003, Petition for Inter Partes Review of U.S. Pat. No. 8,888,701; *Apple, Inc.* (Petitioner) v. *Valencell, Inc.* (Patent Owner), IPR 2017-01704, filed Jun. 30, 2017, pp. 1-109.

Declaration of Brian W. Anthony, PH.D. In Support of Petition for Inter Partes Review of U.S. Pat. No. 8,157,730, Exhibit 1003, Petition for Inter Partes Review of U.S. Pat. No. 8,157,730; *Apple, Inc.* (Petitioner) v. *Valencell, Inc.* (Patent Owner), IPR 2017-01701, filed Jun. 30, 2017, pp. 1-138.

Declaration of Dr. Majid Sarrafzadeh, Exhibit 1003, Petition for Inter Partes Review of U.S. Pat. No. 8,652,040; *Apple, Inc.* (Petitioner) v. *Valencell, Inc.* (Patent Owner), IPR 2017-01703, filed Jun. 30, 2017, pp. 1-87.

Declaration of Dr. Majid Sarrafzadeh, Exhibit 1003, Petition for Inter Partes Review of U.S. Pat. No. 8,652,040; *Apple, Inc.* (Petitioner) v. *Valencell, Inc.* (Patent Owner), IPR 2017-01702, filed Jun. 30, 2017, pp. 1-92.

Asada, H., et al., "Mobile Monitoring with Wearable Photoplethysmographic Biosensors," IEEE Engineering in Medicine and Biology Magazine, May/Jun. 2003 Issue, May 1, 2003, pp. 28-40.

Wang, L. et al. "Multichannel Reflective PPG Earpiece Sensor with Passive Motion Cancellation," IEEE Transactions on Biomedical Circuits and Systems, vol. 1, No. 4, Dec. 1, 2007, pp. 235-241.

Bumgardner, W., "Top 8 Walking Speedometers and Odometers", retrieved on Jun. 18, 2014, retrieved from internet: http://walking.about.com/od/measure/tp/speedometer.htm.

Garmin, "Running Watches Heart Rate Monitor", Swim Watch, Heart Rate Monitors Reviews, Oct. 12, 2010, retrieved from internet: http://web.archive.org/web/*/http://heartratemonitors-reviews.com/category/swim-watch/.

Han et al. "Artifacts in wearable photoplethysmographs during daily life motions and their reduction with least mean square based active noise cancellation method," Computers in Biology and Medicine 42 (2012), Published Dec. 27, 2011, Elsevier Ltd., pp. 387-393.

Poh, Ming-Zher et al., "Non-contact, automated cardiac pulse measurements using video imaging and blind source separation." Optics Express, vol. 18, No. 10, May 7, 2010, pp. 1-13.

* cited by examiner

REDUCTION OF PHYSIOLOGICAL METRIC ERROR DUE TO INERTIAL CADENCE

RELATED APPLICATIONS

This application is a Continuation Application of U.S. application Ser. No. 16/146,362, filed 28 Sep. 2018, which is a Continuation Application of U.S. application Ser. No. 14/370,689, filed 3 Jul. 2014, now patented as U.S. patent Ser. No. 10/349,844, which National Phase of International Application PCT/US2012/071594 filed 24 Dec. 2012, which in turn claims benefit of U.S. Provisional Application No. 61/586,884, filed 16 Jan. 2012. The disclosures of each of these references are incorporated in their entireties by reference herein.

BACKGROUND

Personal health monitors provide users with the ability to monitor their overall health and fitness by enabling the user to monitor heart rate or other physiological information during exercise, athletic training, rest, daily life activities, physical therapy, etc. Such devices are becoming increasingly popular as they become smaller and more portable.

A heart rate monitor represents one example of a personal health monitor. A common type of heart rate monitor uses a chest strap that includes surface electrodes to detect muscle action potentials from the heart. Because such surface electrodes provide a relatively noise free signal, the information produced by monitors that use surface electrodes is relatively accurate. However, most users find chest strap monitors uncomfortable and inconvenient.

Another type of monitor uses photoplethysmograph (PPG) sensors disposed in an ear bud. The ear provides an ideal location for a monitor because it is a relatively immobile platform that does not obstruct a person's movement or vision. PPG sensors proximate the ear may have, e.g., access to the inner ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning). The ear is also at or near the point of the body's exposure to environmental breathable toxins of interest (volatile organic compounds, pollution, etc.), noise pollution experienced by the ear, lighting conditions for the eye, etc. Further, as the ear canal is naturally designed for transmitting acoustical energy, the ear provides a good location for monitoring internal sounds, such as the heartbeat, breathing rate, mouth motion, etc.

PPG sensors measure the relative blood flow using an infrared or other light source that projects light that is ultimately transmitted through or reflected off tissue, and is subsequently detected by a photodetector and quantified. For example, higher blood flow rates result in less light being absorbed, which ultimately increases the intensity of the light that reaches the photodetector. By processing the signal output by the photodetector, a monitor using PPG sensors may measure the blood volume pulse (the phasic change in blood volume with each heartbeat), the heart rate, heart rate variability, and other physiological information.

PPG sensors are generally small and may be packaged such that they do not encounter the comfort and/or convenience issues associated with other conventional health monitors. However, PPG sensors are also highly sensitive to noise, and thus are more prone to accuracy problems. For example, a motion component of a user, e.g., a step rate of a jogger, is often as strong as or stronger than a heart rate component, which may corrupt a heart rate measurement. U.S. Pat. No. 7,144,375, which discloses using an accelerometer as a motion reference for identifying the potential step rate component(s) of a PPG sensor output, provides one possible solution to this problem. When the step rate is close to the heart rate, the '375 patent teaches spectrally transforming the step rate and heart rate waveforms, e.g., over a window of samples, respectively provided by the step rate and heart rate sensors to create a step rate spectrum and a heart rate spectrum. If the spectral transform operation uses a 6 s window, the average latency incurred for the transform operation is 3 s. After performing the spectral transform, the '375 patent spectrally subtracts the heart rate and step rate spectrums. The '375 patent further keeps a history of the top ten peaks from the output of the spectral subtraction to perform various statistical analyses in order to achieve the desired accuracy before making a decision regarding whether there is a cross-over between the heart rate and the step rate, and before making a decision regarding which spectral peak corresponds to the heart rate. Thus, the post-transform operations implemented by the '375 patent incur an additional processing latency, e.g., of ten seconds, which is undesirable. Thus, there remains a need for alternative solutions that provide an accurate heart rate with less latency when the step rate is close to the heart rate.

SUMMARY

The solution disclosed herein removes a step rate component from a measured heart rate by using one or more filtering techniques when the step rate is close to the heart rate. In general, a difference between the step rate and the heart rate is determined, and the step rate is filtered from the heart rate based on a function of the difference.

In one exemplary embodiment a step rate processor computes a step rate of a user based on a waveform provided by a step rate sensor, and a heart rate processor computes a first heart rate of the user based on a waveform provided by a heart rate sensor. A noise processor then computes a difference between the step rate and the heart rate, computes a second heart rate of the user as a function of the difference, and outputs the second heart rate. For example, the noise processor may filter the heart rate as a function of the difference.

More broadly, an exemplary physiological monitor comprises an inertial sensor, an inertial processor, a physiological sensor, a physiological processor, and a noise processor. The inertial processor computes an inertial cadence of a user based on an inertial waveform provided by the inertial sensor. The physiological processor computes a first physiological metric of the user based on a physiological waveform provided by the physiological sensor. The noise processor computes a difference between the inertial cadence and the first physiological metric, computes a second physiological metric as a function of the difference, and outputs the second physiological metric.

An exemplary method reduces noise in data output by a physiological monitor. To that end, the method includes computing an inertial cadence of a user based on an inertial waveform provided by an inertial sensor in the physiological monitor, and computing a first physiological metric of the user based on a physiological waveform provided by a physiological sensor in the physiological monitor. Subsequently, the method computes a difference between the inertial cadence and the first physiological metric, computes a second physiological metric as a function of the difference, and outputs the second physiological metric.

Because the solution disclosed herein processes only the current spectrally transformed data, e.g., the current step rate and heart rate spectrums, the present invention essentially eliminates the post-transform latency incurred by the '375 patent. Thus, the solution disclosed herein provides sufficient accuracy without the undesirable latency associated with the prior art.

DETAILED DESCRIPTION

Figure 1:
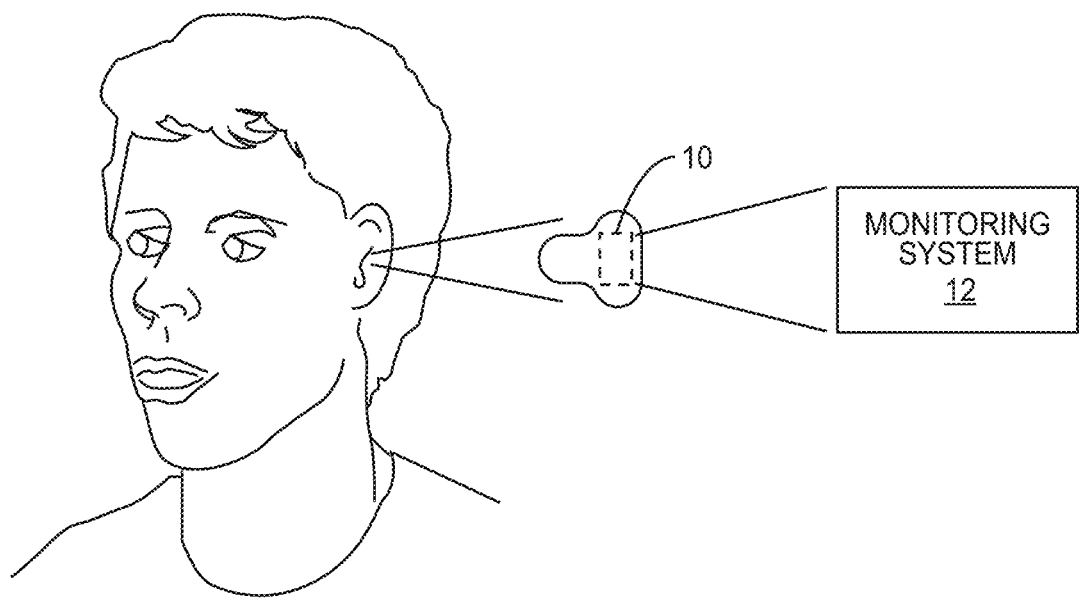
FIG. 1 shows an exemplary heart rate monitor disposed in an ear bud.

The techniques disclosed herein improve the accuracy of the results achieved when processing data, e.g., heart rate data, provided by a physiological sensor. FIG. 1 shows an exemplary monitoring system 12 disposed in an ear bud 10. The ear bud 10 may comprise a wireless or wired ear bud that communicatively couples to a remote device, e.g., a music player, a smart phone, a personal data assistant, etc. The monitoring system 12 monitors the heart rate and/or other physiological metrics, and outputs such physiological information to the user and/or to other processing functions. While the monitoring system 12 disclosed herein is presented as being part of an ear bud 10, it will be appreciated that monitoring system 12 may be disposed into any device that secures to the body of a user, e.g., a device that secures to an ear, finger, toe, limb, wrist, nose, etc. In some embodiments, the device may comprise a patch, e.g., a bandage, designed to attach the system 12 to any desired location on the user's body.

Figure 2:
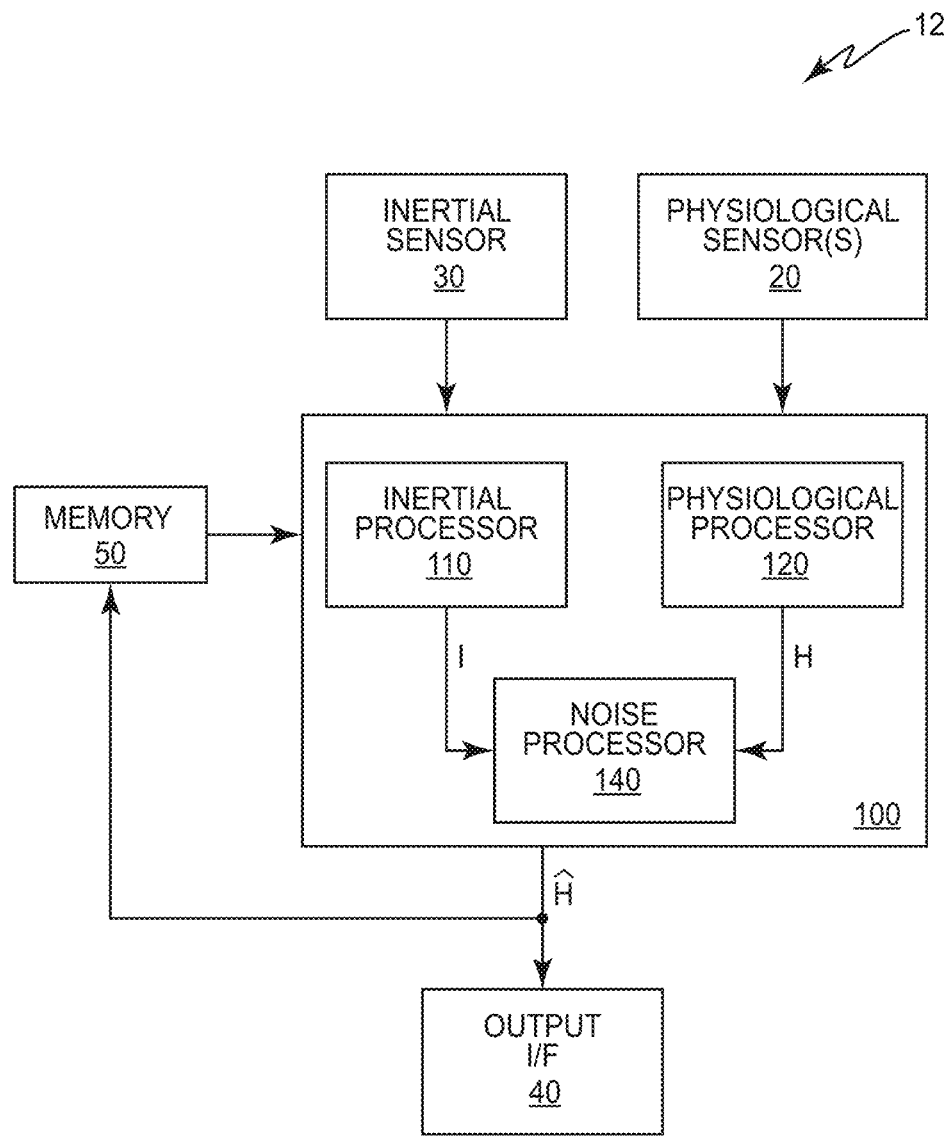
FIG. 2 shows a block diagram of an exemplary physiological monitoring system disposed in a housing.

FIG. 2 shows a block diagram of an exemplary monitoring system 12 according to one exemplary embodiment. System 12 comprises a processor 100 coupled to one or more physiological sensors 20 and one or more inertial sensors 30, an output interface 40, and memory 50. Physiological sensor(s) 20 produce a physiological waveform responsive to the physiological state of the user. Inertial sensor(s) 30 produce an inertial waveform responsive to the movement of the user. An exemplary inertial sensor includes, but is not limited to, an accelerometer, an optical emitter/detector pair, an optical detector, a CCD camera, a piezoelectric sensor, a thermal sensor, or any type of sensor capable of capturing motion information. Exemplary optical emitters comprise one or more light emitting diodes, laser diodes, organic light-emitting diodes, miniature light emitters, electromagnetic emitters, etc. It will be appreciated that the sensors disclosed herein are not limited to optical wavelengths of the electromagnetic spectrum. In some embodiments, emitters and/or detectors configured for shorter or longer wavelengths may be used to accommodate shorter or longer wavelengths in the electromagnetic spectrum. The optical detector may comprise a photodetector, an electromagnetic detector, a photodiode, etc. Processor 100 processes the physiological and inertial waveforms using the technique(s) disclosed herein, along with information stored in memory 50, to remove an inertial cadence from a heart rate and/or one or more physiological metrics. Output interface 40 outputs the determined physiological metric(s). It will be appreciated that output interface may comprise a transceiver for transmitting the data output by the processor 100 to a remote device. Alternatively or additionally, the output interface may provide the output data to a user interface, e.g., a display, a database, another processor, and/or a processing function.

While the physiological sensors 20 may comprise any known physiological sensor, the physiological sensor(s) 20 in exemplary embodiments comprise photoplethysmograph (PPG) sensors that generate an electrical physiological waveform responsive to detected light intensity. PPG sensors comprise light intensity sensors that generally rely on optical coupling of light into the blood vessels. As used herein, the term "optical coupling" refers to the interaction or communication between excitation light entering a region and the region itself. For example, one form of optical coupling may be the interaction between excitation light generated from within a light-guiding ear bud 10 and the blood vessels of the ear. Light guiding ear buds are described in co-pending U.S. Patent Application Publication No. 2010/0217102, which is incorporated herein by reference in its entirety. In one embodiment, the interaction between the excitation light and the blood vessels may involve excitation light entering the ear region and scattering from a blood vessel in the ear such that the intensity of the scattered light is proportional to blood flow within the blood vessel. Another form of optical coupling may result from the interaction between the excitation light generated by an optical emitter within the ear bud 10 and the light-guiding region of the ear bud 10.

Processor 100 comprises an inertial processor 110, physiological processor 120, and noise processor 140. Inertial processor 110 determines an inertial cadence I, e.g., a step rate, from the inertial waveform using any known means. The determined inertial cadence may include the true inertial cadence as well as one or more harmonics of the true inertial cadence, e.g., the ½x, ½x, and 2x harmonics of the true inertial cadence. For example, the inertial processor may spectrally transform the inertial waveform to generate an inertial spectrum, and set the inertial cadence to the frequency of the largest peak of the inertial spectrum. It will be appreciated that other methods may alternatively be used to determine the inertial cadence. Physiological processor 120 determines one or more physiological metrics H, e.g., a heart rate, from the physiological waveform, as discussed further herein. The determined physiological metric may also refer to a physiological assessment computed from one or more physiological metrics. Noise processor 140 filters the determined metric(s) to remove the inertial cadence, and therefore, to produce a revised physiological metric H having an improved accuracy.

For simplicity, the following describes the processor 100 in terms of a noise processor 140 that determines a heart rate by removing a step rate by using one or more filtering techniques when the step rate determined by the inertial processor 110 is close to the heart rate determined by the physiological processor 120. In general, a difference between the step rate and the heart rate is determined, and the step rate is filtered from the heart rate based on a function of the difference. It should be noted, however, that the physiological processor 120, and thus processor 100, may alternatively or additionally determine other physiological metrics, e.g., a respiration rate, a heart rate variability (HRV), a pulse pressure, a systolic blood pressure, a diastolic blood pressure, a step rate, an oxygen uptake (VO2), a maximal oxygen uptake (VO2 max), calories burned, trauma, cardiac output and/or blood analyte levels including percentage of hemoglobin binding sites occupied by oxygen (SPO2), percentage of methomoglobins, a percentage of carbonyl hemoglobin, and/or a glucose level. Alternatively or additionally, processor 100 may determine and filter one or more physiological assessments, e.g., a ventilatory threshold, lactate threshold, cardiopulmonary status, neurological status, aerobic capacity (VO2 max), and/or overall health or fitness. Further, it will be appreciated that the processor 100 may additionally or alternatively remove other inertial cadences, e.g., rhythmic head movements, body movements (e.g., arm movements, weight lifting, etc.), etc., from the heart rate.

Figure 3:
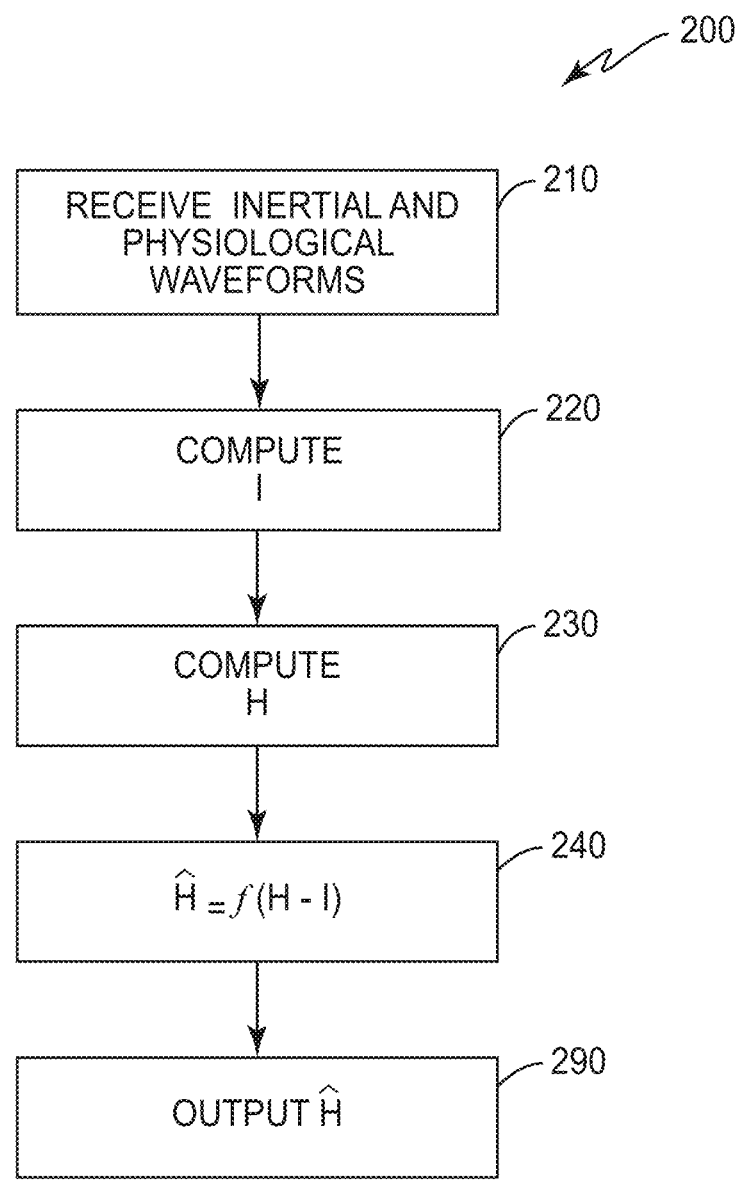
FIG. 3 shows an exemplary process for removing an inertial cadence from a physiological metric.

FIG. 3 shows an exemplary method 200 that may be implemented by processor 100 to compute an output heart rate. After processor 100 receives the inertial and physiological waveforms from the sensor(s) 20 and 30 (block 210), the inertial processor 110 determines a step rate I (block 220), and the physiological processor 120 determines a first estimate H of the heart rate (block 230). The noise processor 140 computes a revised estimate Ĥ of the heart rate as a function of the difference between the step rate and the heart rate (block 240), and subsequently outputs the revised heart rate estimate H to output interface 40 (block 290). It will be appreciated that processor 100 may also store the revised heart rate estimate Ĥ in memory 50, e.g., so that it may be used in subsequent calculations.

Figure 4:
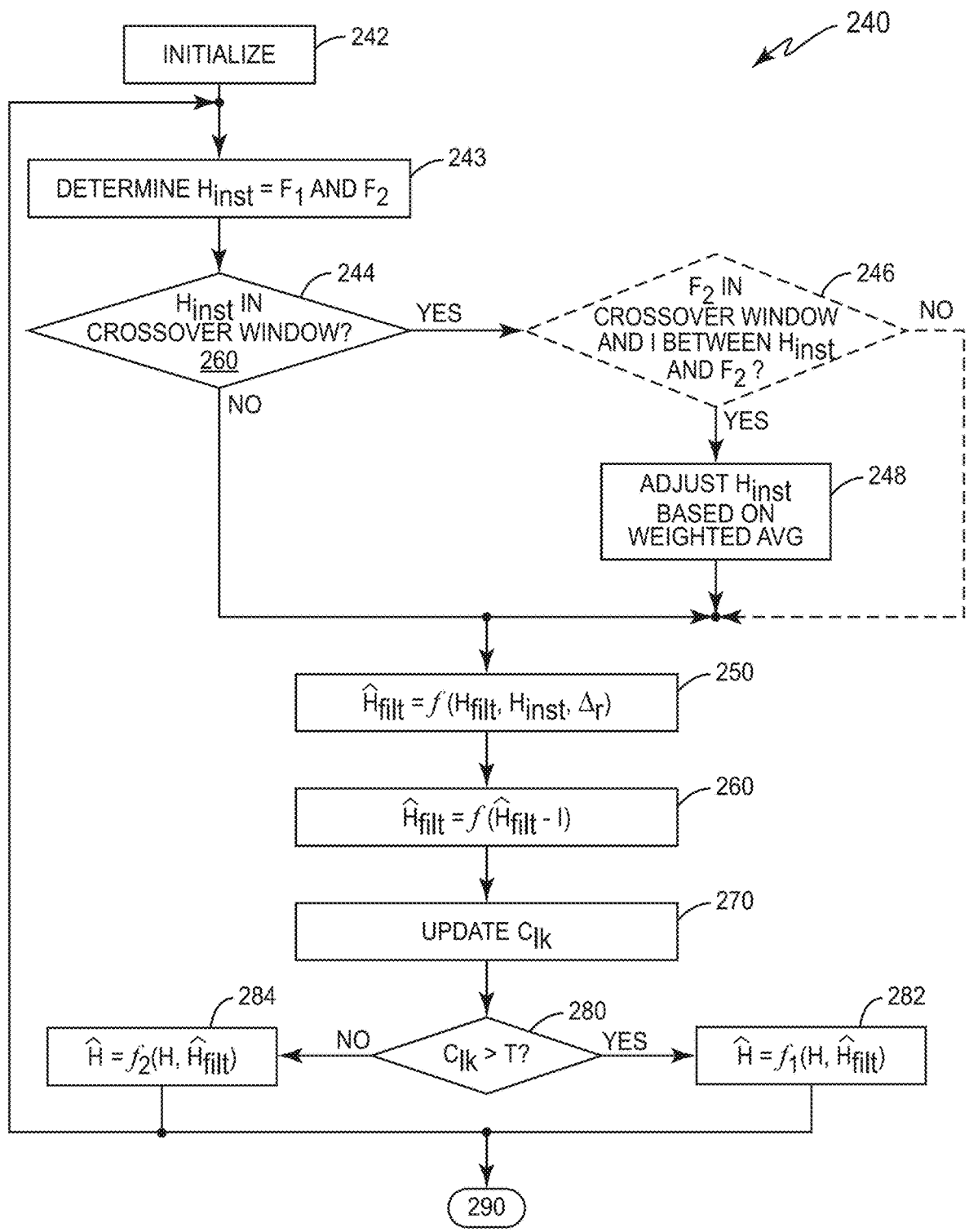
FIG. 4 shows another exemplary process for removing the inertial cadence from the physiological metric.

FIG. 4 shows an exemplary method 240 for computing the revised heart rate Ĥ as a function of the difference between the step rate and the first heart rate. The exemplary method 240 of FIG. 4 includes multiple levels, where a first level includes block 242, a second level includes blocks 244 to 248, a third level includes block 250, a fourth level includes block 260, a fifth level includes block 270, and a sixth level includes blocks 280 to 284. It will be appreciated, however, that some exemplary embodiments may implement one or more of these levels, as described further herein, and/or that the present invention does not require each level to be implemented in the order shown in FIG. 4.

The first level (blocks 242 and 243) comprises an initialization level, where the heart rate processor 120 and/or noise processor 140 initializes and/or determines one or more variables useful for determining the output heart rate based on pre-determined values, values stored in memory, and measured information (blocks 242 and 243), e.g., an instantaneous heart rate $H_{inst}$, a filtered heart rate $H_{filt}$, a lock count $C_{lk}$, a second (or output) heart rate H, etc. For example, to determine $H_{inst}$, heart rate processor 120 comprises a spectral transformer 122 (FIG. 5) that spectrally transforms the physiological waveform output by the heart rate sensor(s) 20 to generate a physiological spectrum. For example, the spectral transformer 122 may transform the heart rate waveform over a window of samples, e.g., 6 s. It will be appreciated that such a transform operation incurs a latency half the length of the window, e.g., 3 s. The heart rate processor 120 initializes the first heart rate by identifying the frequency $F_1$ of the spectral peak of the physiological spectrum having the largest amplitude as an initial instantaneous heart rate $H_{inst}$, where the initial instantaneous heart rate corresponds to the first heart rate (block 243). The heart rate processor 1120 may further identify the frequency $F_2$ of the spectral peak of the physiological spectrum having the next largest amplitude. Alternatively or additionally, a filtered heart rate may be initialized, e.g., by retrieving a previously determined filtered heart rate from memory 50 or by setting $H_{filt}$ to an empirically determined value, e.g., 83. Further, $C_{lk}$ may be initialized by setting it equal to zero, where $C_{lk}$ represents, e.g., the number of successive frames where the difference between the heart rate and the step rate satisfies a predetermined threshold. Noise processor 140 may also determine an initial second (or output) heart rate H, where the second heart rate represents the heart rate ultimately output by the noise processor 140. In some cases, the processor 140 may set the initial H to an empirically determined value, e.g., 83. Alternatively or additionally, the noise processor 140 may initialize H to the Ĥ value from a previous frame after the first iteration through the process 240.

The second level (blocks 244 to 248) determines an instantaneous heart rate as a function of a difference between an initial instantaneous heart rate and the step rate, and particularly addresses the scenario when the results of spectral subtraction wipe out the primary spectral peak typically used to determine the instantaneous heart rate. More particularly, the second level determines whether the step rate I provided by inertial processor 110 is close to the initial instantaneous heart rate $H_{inst}$ by determining whether the initial instantaneous heart rate is within a crossover window (block 244), and adjusts the instantaneous heart rate based on that determination. For example, noise processor 140 may determine whether the initial $H_{inst}$ is within the crossover window by determining whether the difference between the step rate I and the initial $H_{inst}$ is less than or equal to a threshold $T_w$, e.g., $T_w=8$. In one embodiment, noise processor 140 adjusts the initial $H_{inst}$ only when the initial $H_{inst}$ is within the crossover window, where the adjustment is based on a weighted average of the frequencies of two or more of the spectral peaks provided by the spectral transformer 122 (block 248). For example, noise processor 140 may compute a weight w according to:

$$w = \frac{M_1}{M_1 + M_2}, \quad (1)$$

where $M_1$ represents the magnitude of the largest spectral peak of the physiological spectrum and $M_2$ represents the magnitude of a second spectral peak of the physiological spectrum, e.g., the next largest spectral peak. The noise processor 140 then adjusts the instantaneous heart rate by computing a weighted average of the frequencies of the two spectral peaks, e.g., according to:

$$H_{inst} = wF_1 + (1-w)F_2, \quad (2)$$

where $F_1$ represents the frequency of the largest spectral peak (and corresponds to the initial instantaneous heart rate), and $F_2$ represents the frequency of the second spectral peak.

In some embodiments, the second level may also optionally determine whether the frequency $F_2$ of the second spectral peak of the physiological spectrum is also in the crossover window and whether the step rate I is between the initial $H_{inst}$ and $F_2$ (block 246) when the condition of block 244 is satisfied. For example, the noise processor 140 may determine whether $F_2$ is within the crossover window by determining whether the difference between $F_2$ and I is less than or equal to a threshold, e.g., 8. Further, the noise processor 140 may determine whether I is between $F_2$ and the initial $H_{inst}$ by determining whether $sign(H_{inst}-I) \neq sign(F_2-I)$. In any event, for this example, noise processor 140 executes the operation of block 248 only when the conditions of blocks 244 and 246 are both satisfied.

Figure 5:
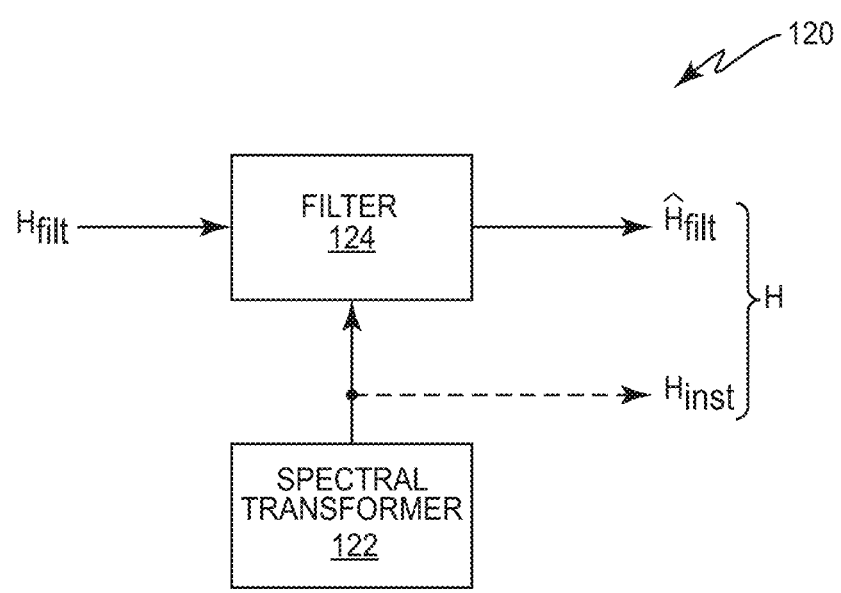
FIG. 5 shows an exemplary block diagram for the physiological processor of FIG. 2.

The third level (block 250) filters the instantaneous heart rate using rate limits. More particularly, the third level computes a revised filtered heart rate $\hat{H}_{filt}$ as a function of a current filtered heart rate $H_{filt}$, the instantaneous heart rate $H_{inst}$ output by the second level, and a rate limit $\Delta_r$. For this embodiment, the heart rate processor 120 may further include a filter 124, as shown in FIG. 5. In general, after comparing $H_{inst}$ to $H_{filt}$, which may be retrieved from memory 50 or provided by initialization block 242, filter 124 computes the revised filtered heart rate estimate $\hat{H}_{filt}$ as a function of $H_{filt}$, $H_{inst}$, and the rate limit $\Delta_r$ based on the comparison, where $\Delta_r$ may also be retrieved from memory 50. In one exemplary embodiment, when $H_{inst} \geq H_{filt}$, filter 124 computes the revised filter estimate $\hat{H}_{filt}$ according to:

$$\hat{H}_{filt} = H_{filt} + \min(\Delta_{r+}, H_{inst} - H_{filt}) \quad (3)$$

where $\Delta_{r+}$ represents an increasing rate limit. However, when $H_{inst} < H_{filt}$, filter 124 computes the revised filter estimate $\hat{H}_{filt}$ according to:

$$\hat{H}_{filt} = H_{filt} + \max(\Delta_{r-}, H_{inst} - H_{filt}), \quad (4)$$

where $\Delta_{r-}$ represents a decreasing rate limit. As used herein, the rate limit represents a limit to the rate of change for the heart rate. For example, the rate limit may represent the rate of change in beats per minute (BPM) that the heart rate may experience in a 1 second frame period. Such a rate limit may be determined based on empirical evidence, and is generally predetermined. It will be appreciated that the rate limit may be expressed as the rate of change experienced for any length frame period, where for example, the rate limit in BPM/s is multiplied by the length of the frame period (in seconds). Additional details for the implementation of block 250 may be found in U.S. Provisional Application Ser. No. 61/586,874 filed concurrently herewith and titled "Physiological Metric Estimation Rise and Fall Limiting," which is incorporated by reference herein in its entirety.

In the fourth level (block 260), the noise processor 140 biases the filtered heart rate toward the step rate to minimize wandering due to blindness during a crossover. To that end, the noise processor 140 further adjusts the revised filter estimate $\hat{H}_{filt}$ as a function of the differenced between the step rate and $\hat{H}_{filt}$. For example, the noise processor 140 may determine whether the revised filter estimate $\hat{H}_{filt}$ output by block 250 is within a crossover window by comparing the difference between $\hat{H}_{filt}$ and I to a threshold, e.g., abs $(I-\hat{H}_{filt}) \leq 8$. If $\hat{H}_{filt}$ is within the crossover window, noise processor 140 may further adjust $\hat{H}_{filt}$ as a function of the difference between $\hat{H}_{filt}$ and I. For example, the noise processor 140 may further adjust $\hat{H}_{filt}$ according to:

$$\hat{H}_{filt} = \hat{H}_{filt} + 0.5 sign(1 - \hat{H}_{filt}). \quad (5)$$

In the fifth level (block 270), the noise processor 140 counts the number of successive frames where the heart rate is within a crossover window. To that end, the noise processor updates a lock count $C_{lk}$ as a function of the difference between I and $\hat{H}_{filt}$ output by block 260, where $C_{lk}$ represents, e.g., the number of successive frames where the difference between $\hat{H}_{filt}$ and I satisfy a threshold requirement. For example, $C_{lk}$ is compared to 0 for equality (e.g., $C_{lk}=0$), and when abs $(H_{filt}-I) < 6$, noise processor 140 may set $C_{lk}=1$. However, when $C_{lk}>0$, and when abs $(H_{filt}-I) > 6$, noise processor 140 may set $C_{lk}=0$, and when $C_{lk}>0$, and when abs $(H_{filt}-I) \leq 6$, noise processor 140 may increment $C_{lk}$, e.g., set $C_{lk}=C_{lk}+1$.

In the sixth level (blocks 280 to 284), the noise processor 140 filters the oscillations of the instantaneous heart rate that occur during a crossover sustained for a number of successive frames. For example, the $\hat{H}_{filt}$ output by block 260 is further filtered responsive to a comparison between the lock count and a threshold $T_c$ to generate the second (or output) heart rate $\hat{H}$ to be output to the output interface 40. For example, if $C_{lk}>T_c$, the output heart rate $\hat{H}$ may be determined as a first function of a previously determined (or initialized) output heart rate H and $\hat{H}_{filt}$, e.g., according to $f_1(H, H_{filt})$ (block 282). In one exemplary embodiment, the first function may comprise:

$$\hat{H} = f_1(H, H_{filt}) = H + (H_{filt} - H)/4 \quad (6)$$

where H represents an initialized second heart rate from block 242, or a previously determined second (or output) heart rate that may, e.g., be retrieved from memory 50. If, however, $C_{lk} \leq T_c$, the output heart rate H may be determined as a second function of the previously determined (or initialized) output heart rate H and $\hat{H}_{filt}$, e.g., according to $f_2(H, H_{filt})$ (block 284). In one exemplary embodiment, the second function may comprise:

$$\hat{H} = f_2(H, \hat{H}_{filt}) = H + (\hat{H}_{filt} - H)/2. \quad (7)$$

It will be appreciated that not all of the six levels of FIG. 4 are required to determine $\hat{H}$ output to the output interface 40. For example, exemplary embodiments may compute the output heart rate using:

- the second and third levels, where the output heart rate comprises the filtered heart rate $\hat{H}_{filt}$ output by filter 124 of FIG. 5 and block 250 of FIG. 4.
- the third and fourth levels, where the output heart rate comprises the filtered heart rate $\hat{H}_{filt}$ output by block 260 of FIG. 4, and the input heart rates comprise e.g., an initial instantaneous heart rate $H_{inst}$ from block 242 of Figure and an initial filtered heart rate $H_{filt}$ obtained from block 242 of FIG. 4 or previously determined and retrieved from memory 50.
- the fourth level, where the output heart rate comprises the filtered heart rate $\hat{H}_{filt}$ output by block 260 of FIG. 4, and the input heart rate comprises, e.g., an initial filtered heart rate $H_{filt}$ obtained from block 242 of FIG. 4 or previously determined and retrieved from memory 50.
- the third, fourth, fifth, and sixth levels, where the output heart rate comprises $\hat{H}$ as output by one of blocks 282 and 284 of FIG. 4, and the input heart rates comprise an initial instantaneous heart rate $H_{inst}$ from block 242 of Figure and an initial filtered heart rate $H_{filt}$ obtained from block 242 of FIG. 4 or previously determined and retrieved from memory 50.
- the fourth, fifth, and sixth levels, where the output heart rate comprises $\hat{H}$ as output by one of blocks 282 and 284 of FIG. 4, and the input heart rate comprises an initial filtered heart rate obtained from block 242 of FIG. 4 or previously determined and retrieved from memory 50.
- the fifth and sixth levels, where the output heart rate comprises $\hat{H}$ as output by one of blocks 282 and 284 of FIG. 4, and the input heart rates comprise an initial second heart rate H obtained from block 242 of FIG. 4 and an initial filtered heart rate obtained from block 242 of FIG. 4 or previously determined and retrieved from memory 50.

the sixth level, where the output heart rate comprises $\hat{H}$ as output by one of blocks 282 and 284 of FIG. 4, and the input heart rates comprise an initial second heart rate H obtained from block 242 of FIG. 4 and an initial filtered heart rate obtained from block 242 of FIG. 4 or previously determined and retrieved from memory 50. In this case, the decision diamond 280 not only considers how the lock count compares to the threshold, but it also considers whether the filtered heart rate is within a crossover window, e.g., by determining whether the difference between $\hat{H}_{filt}$ and I is less than or equal to a threshold $T_w$.

the third, fifth, and sixth levels, where the output heart rate comprises $\hat{H}$ as output by one of blocks 282 and 284 of FIG. 4, and the input heart rates comprise an initial instantaneous heart rate $H_{inst}$ from block 242 of Figure and an initial filtered heart rate $H_{filt}$ obtained from block 242 of FIG. 4 or previously determined and retrieved from memory 50.

It will be appreciated that other combinations not explicitly disclosed herein may also be used to generate the output heart rate.

Figure 6A:
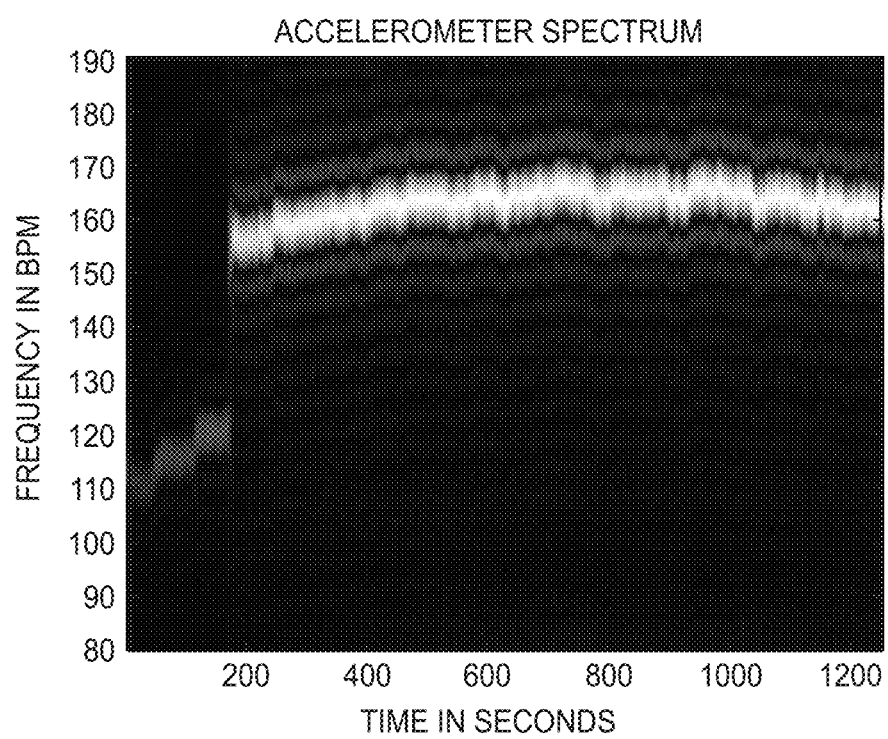
FIGS. 6A-6D show exemplary results of simulated step rate and heart rate spectrums, and the resulting difference spectrums and estimated heart rates.
Figure 6B:
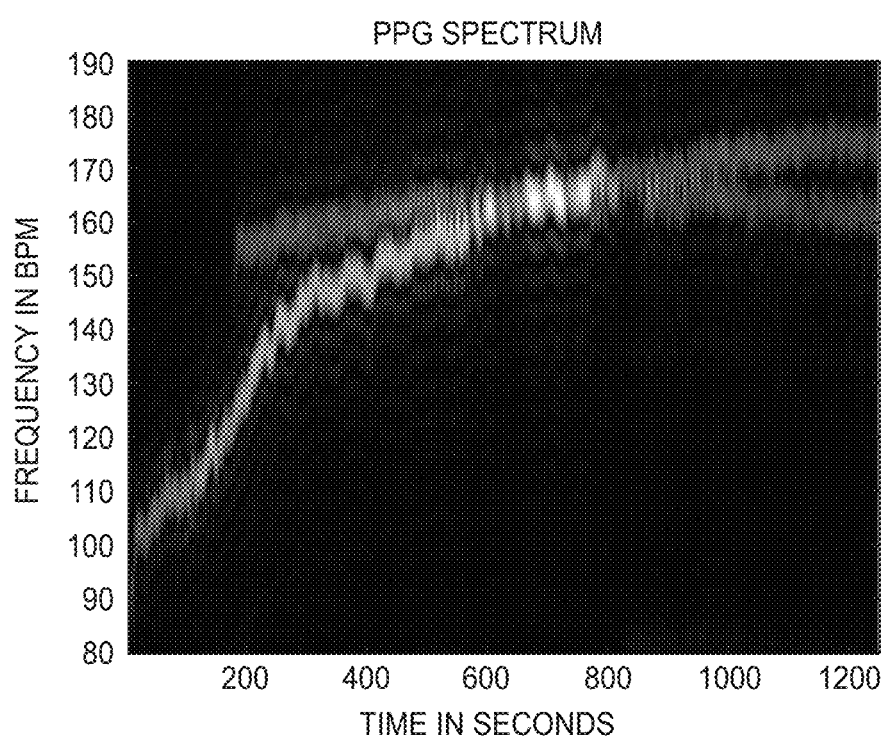
Figure 6C:
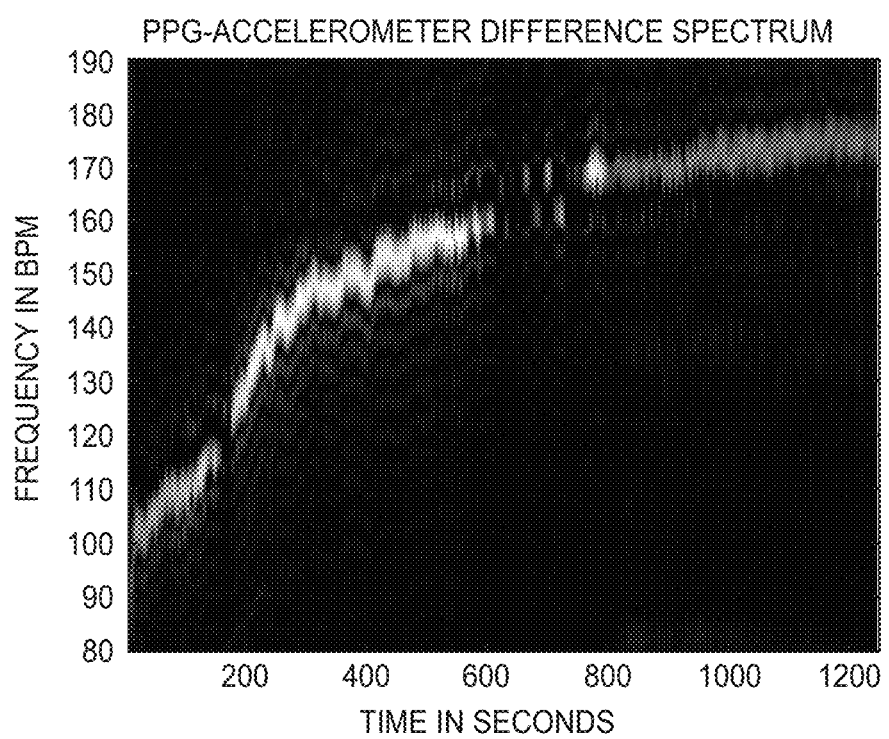
Figure 6D:
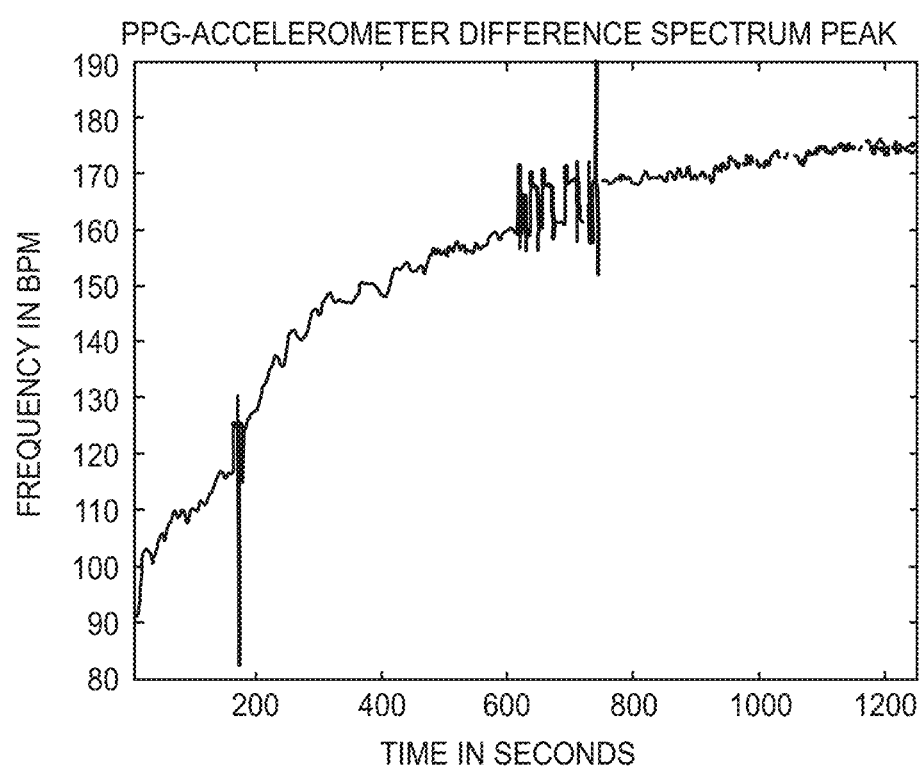

FIGS. 6A-6D and 7 further illustrate both the impact of a step rate on a measured heart rate, and how the solution disclosed herein addresses this problem. First, FIGS. 6A-6D simulate the problems that occur when the step rate and the heart rate are close together. In particular, FIG. 6A shows a step rate spectrum generated responsive to an accelerometer waveform, while FIG. 6B shows a heart rate spectrum generated responsive to a waveform output by a PPG sensor, and thus includes both step rate and heart rate elements. FIG. 6C shows the spectrum produced when the accelerometer spectrum of FIG. 6A is simply subtracted from the heart rate spectrum of FIG. 6B. As shown in FIG. 6C, when the step rate is close to the heart rate, e.g., between 600 and 800 s, the heart rate is attenuated. Thus, while simple spectral subtraction removes the step rate component, it also corrupts the heart rate measurements subsequently obtained from the heart rate spectrum. In particular, FIG. 6D shows how the peak frequency of the difference spectrum of FIG. 6C has large oscillating errors in the crossover window.

Figure 7:
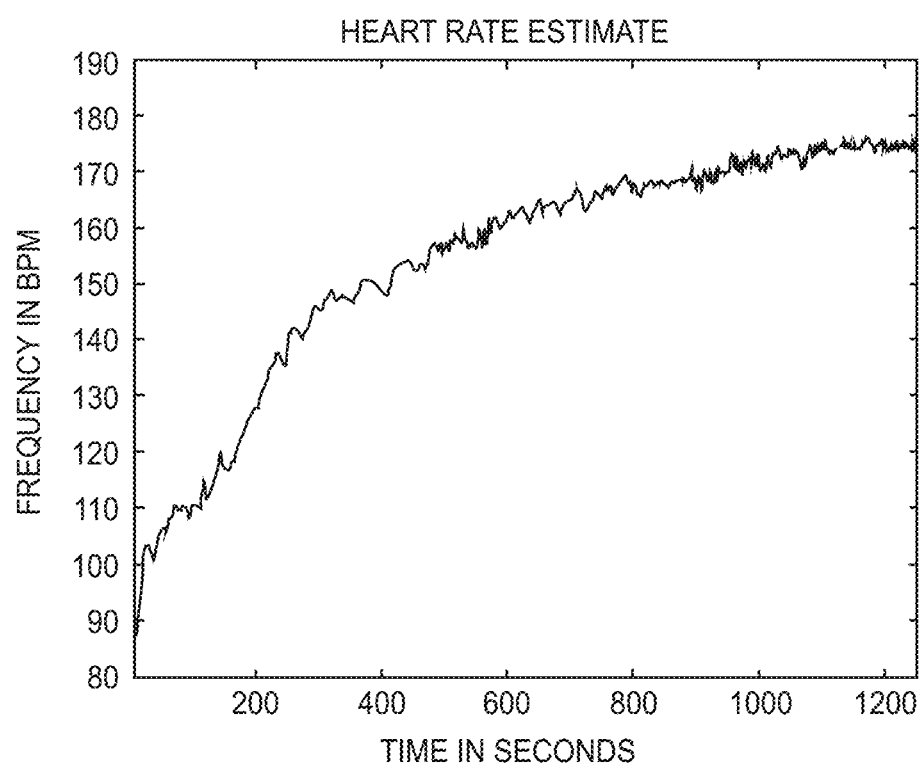
FIG. 7 show an exemplary result of a simulation used to estimate a heart rate according to the solution disclosed herein.

FIG. 7 shows the simulation results when the heart rate is estimated using the techniques disclosed herein, e.g., the techniques of FIG. 4. As shown in FIG. 7, the errors around the crossover regions have nearly disappeared, which results in a more accurate heart rate estimate.

The solution disclosed herein provides an accurate heart rate estimate, as shown for example by the simulated results of FIG. 7, without incurring the latency problems associated with the known prior art solution. In particular, because the solution disclosed herein does not require multiple spectrums or statistics to be buffered in a look-ahead fashion in order to detect the initial crossover, which leads to an undesirable latency, the solution disclosed herein avoids the latency problems associated with the prior art without sacrificing accuracy.

While the present invention is described in terms of PPG sensors, it will be appreciated that sensors 20 may comprise any sensor able to generate a physiological waveform, e.g., an electroencephalogram (EEG) waveform, and electrocardiogram (ECG) waveform, a radio frequency (RF) waveform, an electro-optical physiological waveform, and electro-photoacoustic waveform including a photoacoustic waveform, an electro-mechanical physiological waveform, and/or an electro-nuclear physiological waveform.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A heart rate monitor for sensing a heart rate of a user, the heart rate monitor comprising:
 a photoplethysmograph (PPG) sensor configured to:
   sense light scattered from a body of the user; and
   provide PPG information responsive to the sensed light;
 a step rate sensor configured to:
   sense motion from the user; and
   provide motion information responsive to the sensed motion;
 at least one processor circuit configured to:
   determine a step rate of a user from the motion information provided by the step rate sensor;
   determine an initial instantaneous heart rate from the PPG information provided by the PPG sensor and the motion information provided by the step rate sensor;
   determine a revised heart rate, responsive to whether the initial instantaneous heart rate is within a first crossover window relative to the step rate, from the initial instantaneous heart rate and the step rate;
   determine an output heart rate from the revised heart rate; and
   output the output heart rate.

2. The heart rate monitor of claim 1 wherein the at least one processor circuit determines the revised heart rate by:
 determining a second instantaneous heart rate, responsive to whether the initial instantaneous heart rate is within the first crossover window relative to the step rate, from the initial instantaneous heart rate and the step rate; and
 determine the revised heart rate from the second instantaneous heart rate.

3. The heart rate monitor of claim 2:
 wherein the at least one processor circuit is further configured to compute a difference between the initial instantaneous heart rate and the step rate; and
 wherein the at least one processor circuit determines the second instantaneous heart rate by determining the second instantaneous heart rate, responsive to whether the difference is less than a threshold, as a function of the initial instantaneous heart rate.

4. The heart rate monitor of claim 3:
 wherein the at least one processor circuit is further configured to determine a weighted average of frequencies of two or more spectral peaks of the PPG information; and
 wherein the at least one processor circuit determines the second instantaneous heart rate by determining the second instantaneous heart rate as a function of the weighted average when the difference is less than the threshold.

5. The heart rate monitor of claim 1 wherein:
 the initial instantaneous heart rate corresponds to a first frequency of the PPG waveform;
 the at least one processor circuit is further configured to determine whether a second frequency of the PPG waveform corresponding to a second peak of the PPG waveform is within the first crossover window; and the at least one processor circuit further determines the revised heart rate responsive to whether the second frequency is within the first crossover window.

6. The heart rate monitor of claim 5 wherein the at least one processor circuit further determines the revised heart rate responsive to whether the step rate is between the initial instantaneous heart rate and the second frequency.

7. The heart rate monitor of claim 1 wherein the at least one processor circuit determines the revised heart rate by:
   determining whether the revised heart rate is within the first crossover window responsive to a comparison of a difference between the revised heart rate and the step rate to a threshold; and
   when the revised heart rate is within the first crossover window, adjusting the revised heart rate as a function of the difference between revised heart rate and the step rate to generate an adjusted revised heart rate.

8. The heart rate monitor of claim 1 wherein the at least one processor circuit is further configured to determine a number of successive frames where the revised heart rate is within the first crossover window to determine a lock count.

9. The heart rate monitor of claim 8 wherein the at least one processor circuit determines the output heart rate by:
   determining the output heart rate as a first function of an initialized second heart rate and the revised heart rate when the lock count exceeds a threshold; and
   determining the output heart rate as a second function of the initialized second heart rate and the revised heart rate when the lock count does not exceed the threshold; wherein the first function differs from the second function.

10. A method of sensing a heart rate of a user comprising:
    sensing light scattered from a body of the user using a photoplethysmograph (PPG) sensor, said PPG sensor providing PPG information responsive to the sensed light;
    sensing motion from the user using a step rate sensor, said step rate sensor providing motion information responsive to the sensed motion;
    determining a step rate of a user from the motion information provided by the step rate sensor;
    determining an initial instantaneous heart rate from the PPG information provided by the PPG sensor and the motion information provided by the step rate sensor;
    determining a revised heart rate, responsive to whether the initial instantaneous heart rate is within a first crossover window relative to the step rate, from the initial instantaneous heart rate and the step rate;
    determining an output heart rate from the revised heart rate; and
    outputting the output heart rate to the user.

11. The method of claim 10 wherein the determining the revised heart rate comprises:
    determining a second instantaneous heart rate, responsive to whether the initial instantaneous heart rate is within the first crossover window relative to the step rate, from the initial instantaneous heart rate and the step rate; and
    determine the revised heart rate from the second instantaneous heart.

12. The method of claim 11 further comprising computing a difference between the initial instantaneous heart rate and the step rate, wherein the determining the second instantaneous heart rate comprises determining the second instantaneous heart rate, responsive to whether the difference is less than a threshold, as a function of the initial instantaneous heart rate.

13. The method of claim 12 further comprising determining a weighted average of frequencies of two or more spectral peaks of the PPG information, wherein the determining the second instantaneous heart rate comprises determining the second instantaneous heart rate as a function of the weighted average when the difference is less than the threshold.

14. The method of claim 10 wherein the initial instantaneous heart rate corresponds to a first frequency of the PPG waveform, the method further comprising;
    determining whether a second frequency of the PPG waveform corresponding to a second peak of the PPG waveform is within the first crossover window; and
    determining the revised heart rate responsive to whether the second frequency is within the first crossover window.

15. The method of claim 14 wherein the determining the revised heart rate comprises determining the revised heart rate responsive to whether the step rate is between the initial instantaneous heart rate and the second frequency.

16. The method of claim 10 wherein the determining the revised heart rate comprises:
    determining whether the revised heart rate is within the first crossover window responsive to a comparison of a difference between the revised heart rate and the step rate to a threshold; and
    when the revised heart rate is within the first crossover window, adjusting the revised heart rate as a function of the difference between revised heart rate and the step rate to generate an adjusted revised heart rate.

17. The method of claim 10 further comprising determining a number of successive frames where the revised heart rate is within the first crossover window to determine a lock count.

18. The method of claim 17 wherein the determining the output heart rate comprises:
    determining the output heart rate as a first function of an initialized second heart rate and the revised heart rate when the lock count exceeds a threshold; and
    determining the output heart rate as a second function of the initialized second heart rate and the revised heart rate when the lock count does not exceed the threshold; wherein the first function differs from the second function.

* * * * *

UNITED STATES PATENT AND TRADEMARK OFFICE
CERTIFICATE OF CORRECTION

PATENT NO. : 10,631,740 B2  
APPLICATION NO. : 16/694402  
DATED : April 28, 2020  
INVENTOR(S) : Eric Douglas Romesburg Page 1 of 1

It is certified that error appears in the above-identified patent and that said Letters Patent is hereby corrected as shown below:

In the Claims

In Column 10, Line 63, in Claim 5, delete "of the PPG waveform;" and insert --of a PPG waveform;--, therefor.

In Column 12, Line 4, in Claim 11, delete "heart." and insert --heart rate.--, therefor.

In Column 12, Lines 19-20, in Claim 14, delete "of the PPG waveform," and insert --of a PPG waveform,--, therefor.

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*